United States Patent
Ko et al.

(10) Patent No.: US 7,612,228 B2
(45) Date of Patent: Nov. 3, 2009

(54) SYNTHETIC METHOD OF GLYCOL DIESTERS FROM REACTION OF GLYCOL MONOESTERS AND LINEAR ALIPHATIC CARBOXYLIC ACIDS

(75) Inventors: Donghyun Ko, Daejeon (KR); Kwang Ho Park, Daejeon (KR); Sang Gi Lee, Daejeon (KR); Jijoong Moon, Daejeon (KR); Sungshik Eom, Daejeon (KR); Dae Sun Rew, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 12/241,521

(22) Filed: Sep. 30, 2008

(65) Prior Publication Data

US 2009/0023946 A1    Jan. 22, 2009

Related U.S. Application Data

(62) Division of application No. 11/209,255, filed on Aug. 23, 2005, now Pat. No. 7,453,008.

(51) Int. Cl.
    *C07C 67/02*   (2006.01)
(52) U.S. Cl. ....................................................... 560/263
(58) Field of Classification Search ........................ None
    See application file for complete search history.

(56) References Cited

U.S. PATENT DOCUMENTS

| 2,820,014 A | * | 1/1958 | Ramsay et al. ............. 508/485 |
| 5,008,126 A | * | 4/1991 | Klemann et al. ............ 426/611 |
| 5,180,847 A | | 1/1993 | Thurman et al. |
| 5,324,853 A | | 6/1994 | Jones |
| 5,645,696 A | | 7/1997 | Woo et al. |
| 2003/0068295 A1 | * | 4/2003 | Rohde et al. ................ 424/76.1 |

FOREIGN PATENT DOCUMENTS

| DE | 3102826 A1 | 8/1982 |
| JP | 49-94621 | 9/1974 |

OTHER PUBLICATIONS

Hector R. de Lima, "Synthesis method for glycol diesters by cactalytic action of metal halides of groups VIII, II, and V (iron, zinc, and antimony", Rev. Soc. Venezolana guim. (1959) (No. 30), 44-51.

* cited by examiner

*Primary Examiner*—Paul A Zucker
(74) *Attorney, Agent, or Firm*—Cantor Colburn LLP

(57) ABSTRACT

A method of synthesizing glycol diester by reacting a linear aliphatic carboxylic acid and a glycol monoester in the presence of a Lewis acid type catalyst is provided. In the method, after introducing the glycol monoester, the linear aliphatic carboxylic acid and the Lewis acid type catalyst into a reactor, the reaction occurs to produce reaction products and water in the reactor; an excess of the linear aliphatic carboxylic acid forms an azeotrope with water during the reaction to be sent to a condenser through a distillation column; the linear aliphatic carboxylic acid and water passed through the condenser are divided into an organic layer and an aqueous layer in an oil water separator; and the organic layer is returned to the distillation column through a material cycling line and water in the aqueous layer is removed through a water removal line. By utilizing reactive distillation technique, water produced during the reaction is rapidly removed, and thus the reaction time can be significantly reduced and the yield of the glycol diester can be maximized.

1 Claim, 1 Drawing Sheet

SYNTHETIC METHOD OF GLYCOL DIESTERS FROM REACTION OF GLYCOL MONOESTERS AND LINEAR ALIPHATIC CARBOXYLIC ACIDS

This application is a divisional application of U.S. patent application Ser. No. 11/209,255, filed Aug. 23, 2005, the disclosure of which is incorporated herein in its entirety by reference.

BACKGROUND OF THE INVENTION

1. Field of the Invention

The present invention relates to a method of synthesizing a glycol ester represented by formula (3) from a glycol monoester represented by formula (1) and a linear aliphatic carboxylic acid represented by formula (2) in the presence of a Lewis acid type catalyst utilizing reactive distillation technique in which a reaction time can be significantly reduced by rapidly removing water produced during the reaction:

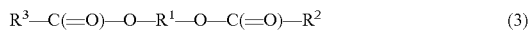

where $R^1$ is a $C_1$-$C_{16}$ alkylidene group, $R^2$ is a $C_1$-$C_{16}$ alkyl group, and $R^3$ is a $C_3$-$C_{16}$ linear alkyl group.

2. Description of the Related Art

Generally, in the case of the same molecular weight, glycol diesters produced by the reaction between glycol monoesters and linear organic acids have superior physical properties than glycol diesters produced by the reaction between glycol monoesters and branched organic acids due to physical properties of the linear organic acids. For example, viscosity, migration-resistance in the application processing test of polymers such as polyvinyl chloride (PVC), and etc.

Glycol diesters are produced through an ester reaction from alcohols and acids in the presence of catalysts, in which water is also produced as a by-product together with the desirable products. During the reaction, water increases over time. In the reversible ester reaction, due to the presence of water, the reaction rate is reduced and the activity of the used Lewis acid catalyst is degraded. Thus, in order to reduce the reaction time by increasing the reaction rate, it is important to rapidly separate and remove water produced during the reaction from reactants. Studies on a method of removing water produced during the reaction, at fastest rate, have been conducted. Also, a method of increasing the yield of glycol esters by optimizing a catalyst and operating conditions, etc. has also been studied. Conventional technologies of synthesizing glycol diesters are as follows.

Japanese Patent Laid-Open Publication No. 49-94621 discloses the reaction of 2,2,4-trimethyl-1,3-pentanediol monoisobutyrate and isobutyric acid using tetraisopropyl titanate as a catalyst. In the method, xylene is used as a solvent and water produced during the reaction is removed using azeotropic distillation. In the publication, it is described that the reaction time is 18 hours which is significantly shortened time compared to 24 hours required in other conventional methods, and the yield of 2,2,4-trimethyl-1,3-pentanediol diisobutyrate is 95%. However, this technology further requires a process of recovering the solvent after the reaction and does not achieve significant reduction in the reaction time.

In DE Pat. No. 3,102,826, isobutyraldehyde is used as a starting material and para-toluenesulfonic acid which is a strong acid is used as a reaction catalyst. As a result, the reaction is completed in only about 4 hours. Although the reaction time is somewhat shortened, the selectivity to 2,2,4-trimethyl-1,3-pentanediol diisobutyrate is 78% and reaction process yield was low (61%).

U.S. Pat. No. 5,180,847 teaches that isobutyraldehyde is used as a starting material and an alkali metal hydroxide which is a strong base is used as a catalyst to produce about 23% of 2,2,4-trimethyl-1,3-pentanediol, about 28% of 2,2,4-trimethyl-1,3-pentanediol monoisobutyrate and 41% of 2,2,4-trimethyl-1,3-pentandiol diisobutyrate. In this case, three useful components can be simultaneously obtained, but when 2,2,4-trimethyl-1,3-pentanediol diisobutyrate is desired as a final product, the yield of the final product is low.

As described above, when a Lewis acid type catalyst is used to increase the yield of glycol diester such as 2,2,4-trimethyl-1,3-pentandiol diisobutyrate, the reaction time is long. Meanwhile, when a strong acid or strong base catalyst is used to shorten the reaction time, the selectivity to glycol diester and the yield thereof are low. Thus, there is a demand for a process capable of maximizing the yield of glycol diester and shortening the reaction time.

The inventors of the present invention discovered that the selectivity to glycol diester can be maximized by using a Lewis acid type catalyst which is a weak acid, for example, tetraisopropyl titanate, tetra-n-butyl titanate, tetra 2-ethylhexyl titanate, etc., and reactive distillation through a distillation column installed in a reactor is utilized to effectively remove water produced during the reaction under the condition that an excess of a linear aliphatic carboxylic acid is used, thereby achieving significant reduction in the reaction time. Thus, the present invention is completed.

SUMMARY OF THE INVENTION

The present invention provides a method of synthesizing a glycol diester from a glycol monoester and a linear aliphatic carboxylic acid using a Lewis acid type catalyst, in which the selectivity to the glycol diester is maximized and the reaction time is significantly reduced, and a novel glycol diester obtained.

According to an aspect of the present invention, there is provided a method of synthesizing a glycol diester, including reacting a linear aliphatic carboxylic acid and glycol monoester in the presence of a Lewis acid type catalyst.

In the method, after introducing the glycol monoester, the linear aliphatic carboxylic acid and a Lewis acid type catalyst into a reactor, the reaction occurs to produce reaction products and water; an excess of the linear aliphatic carboxylic acid forms an azeotrope with water to be sent to a condenser through a distillation column; the linear aliphatic carboxylic acid and water passed through the condenser are divided into an organic layer and an aqueous layer in an oil water separator; and the organic layer is returned to the distillation column through a material cycling line and water in the aqueous layer is removed through a water removal line.

The glycol monoester may be at least one compound selected from the group consisting of compounds having the structure represented by the formula (1) and the linear aliphatic carboxylic acid may be at least one compound selected from the group consisting of compounds having the structure represented by the formula (2).

The amount of the Lewis acid type catalyst added may be 0.2-2.0 parts by weight based on the weight of the glycol monoester, the reaction time may be 2-12 hours, the yield of the glycol diester may be 95% or greater, and the reaction temperature may be 150-250° C.

The distillation column may have 5-20 steps.

The method of the present invention can significantly reduce the reaction time of a glycol diester by properly selecting a reaction catalyst and utilizing reactive distillation technique to effectively separate reactants and water as a by-product.

BRIEF DESCRIPTION OF THE DRAWINGS

The above and other features and advantages of the present invention will become more apparent by describing in detail exemplary embodiments thereof with reference to the attached drawing in which.

DETAILED DESCRIPTION OF THE INVENTION

Figure 1:
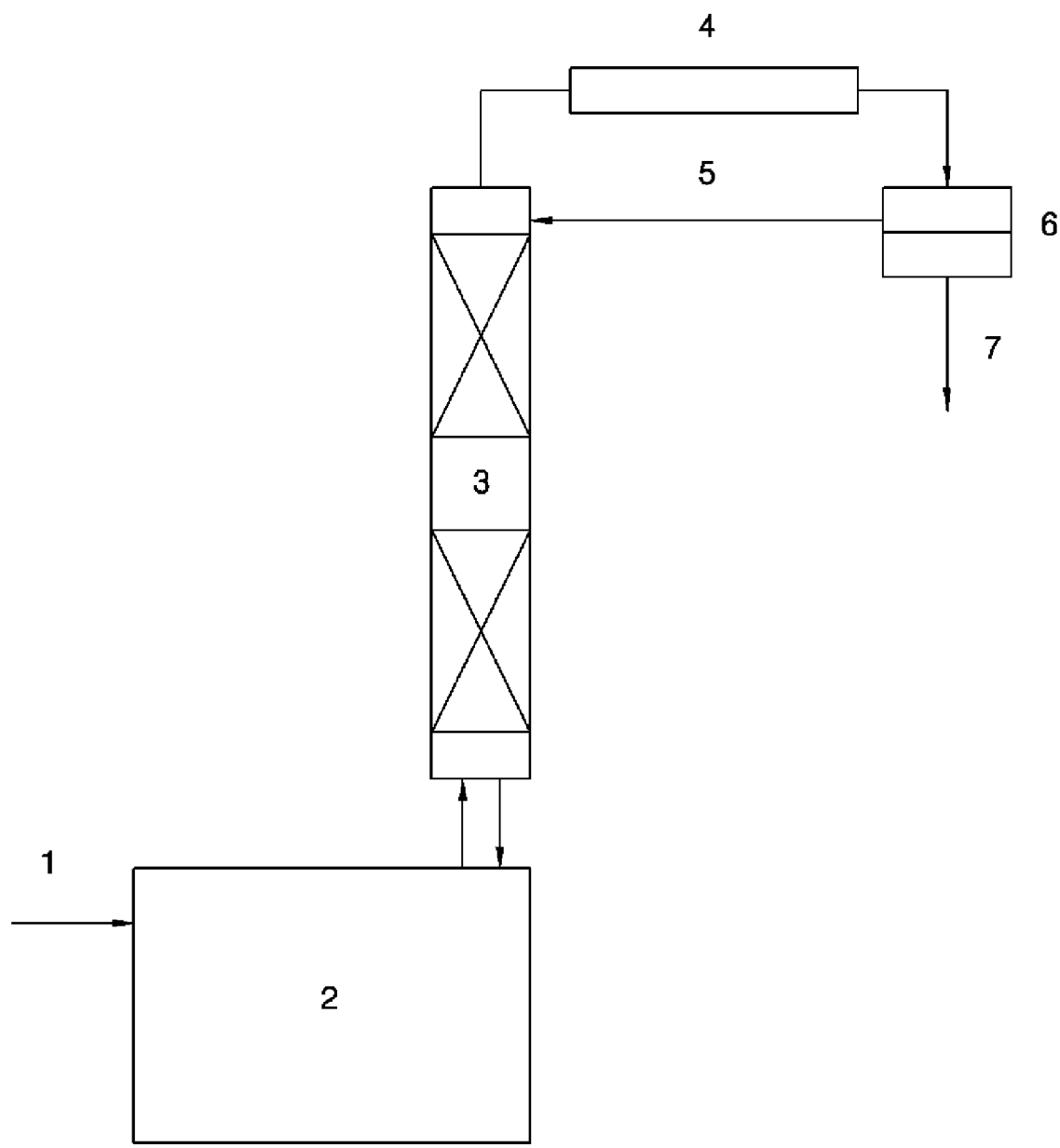
FIG. 1 is a schematic diagram of a reactive distillation device according to an embodiment of the present invention.

Hereinafter, the present invention will be described in greater detail with reference to the attached drawing.

In an embodiment of the present invention, a reactive distillation device capable of simultaneously performing reaction and distillation in an upper portion of which a distillation column is mounted to effectively separate reaction products and water as a by-product is used to reduce the reaction time.

FIG. 1 is a schematic diagram of a reactive distillation device according to an embodiment of the present invention.

A glycol monoester, a linear aliphatic carboxylic acid and a Lewis acid type catalyst are charged into a reactor 2. Then, the reaction occurs to produce reaction products and water as a by-product in the reactor 2. At this time, the linear aliphatic carboxylic acid which is supplied in an excessive amount forms an azeotrope with water to move upward through a distillation column 3. The linear aliphatic carboxylic acid and water pass through a condenser 4 and are divided into an organic layer and an aqueous layer in an oil water separator 6. The organic layer primarily including the linear aliphatic carboxylic acid is returned to the distillation column 3 through a material cycling line 5 to participate in the reaction again and water is continuously removed through a water removal line 7.

In the present invention, the reaction time can be significantly reduced by continuously removing water using the reactive distillation device when the reaction occurs and the selectivity to a glycol diester can be maximized using the Lewis acid type catalyst. Further, since the linear aliphatic carboxylic acid forms an azeoptrope with water, it is not necessary to use an another solvent to form an azeotrope with water which is a by-product of the esterification reaction.

The Lewis acid type catalyst may be any catalyst used in the art. Examples of the Lewis acid type catalyst include, but are not limited to, tetraisopropyl titanate, tetrabutyl titanate, dibutyltin acetate, tin oxalate, phosphoric acid, etc.

A proper reaction time in the reactor 2 is 2-12 hours and may be 4-8 hours. When the reaction time is less than 2 hours, the yield of the glycol diester may be reduced to less than 95%. When the reaction time is greater than 12 hours, the yield of the glycol diester is similar to a desired level, but the reaction time is long, which causes a reduction in productivity.

The yield of the glycol diester is preferably 95% or greater, and more preferably 95-99.99%.

The amount of the catalyst added is preferably 0.2-2.0 parts by weight, and more preferably 0.4-1.5 parts by weight, based on the weight of the glycol monoester.

When the amount of the catalyst added is less than 0.2 part by weight based on the weight of the glycol monoester, the reaction rate is reduced. When the amount of the catalyst added is greater than 2.0 parts by weight, the catalyst cost increases without an increase in the reaction rate.

A reaction temperature of the reactor 2 is preferably 150-250° C., and more preferably 180-230° C.

When the reaction temperature is less than 150° C., the conversion rate is reduced due to decrease in the reaction rate. When the reaction temperature is greater than 250° C., the reaction solution is discoloured.

The distillation column 3 has preferably 5-30 steps, and more preferably 5-20 steps, to effectively separate water produced during the reaction. A tray column or a packing column containing a packing material which show the same separation efficiency as with the distillation column may also be used.

When the number of step is less than 5, effective removal of water is not achieved, and thus the reaction rate is reduced. When the number of step is greater than 30, investment cost and energy increase without an increase in the reaction rate.

After the reaction is completed, the conversion rate of the glycol monoester and the selectivity to the glycol diester and the yield thereof are calculated using Equations 1, 2 and 3:

Conversion rate (%)=[1−(the amount of glycol monoester remained after the reaction/the amount of glycol monoester added before the reaction)]×100  Equation 1

Yield (%)=[(the amount of the resulting glycol diester)/(the amount of glycol monoester added before the reaction)×(the molecular weight of glycol monoester/the molecular weight of glycol diester)]×100  Equation 2

Selectivity (%)=(Yield/Conversion rate)×100.  Equation 3

According to an embodiment of the present invention, there is a glycol diester represented by formula (3):

$$R^3-C(=O)-O-R^1-O-C(=O)-R^2 \quad (3)$$

where $R^1$ is a $C_1$-$C_{16}$ alkylidene group, $R^2$ is a $C_1$-$C_{16}$ alkyl group, and $R^3$ is a $C_3$-$C_{16}$ linear alkyl group.

In formula (3), $R^1$ and $R^2$ may be each independently a linear or branched group. Preferably, $R^1$ is a branched alkylidene, $R^2$ is methyl, ethyl, propyl, isopropyl, butyl, isobutyl, pentyl, isopentyl, hexyl or heptyl, and $R^3$ is propyl, butyl, hexyl, heptyl or octyl. More preferably, the glycol diester is 2,2,4-trimethyl-1,3-pentanediol monobutyrate monoisobutyrate, 2,2,4-trimethyl-1,3-pentanediol mono-2-ethylhexanoate monobutyrate, neopentyl glycol monobutyrate monoisobutyrate or neopentylglycol mono-2-ethylhexanoate monobutyrate.

In the glycol diester represented by formula (3), it is preferred that $R^1$ is a 2,2,4-trimethyl-1,3-pentylidene group, $R^2$ is a $C_1$-$C_{16}$ alkyl group, $R^3$ is a $C_3$-$C_{16}$ linear alkyl group, and $R^2$ and $R^3$ have different substituents from each other.

Alternatively, in the glycol diester represented by formula (3), it is preferred that $R^1$ is a 2,2,4-trimethyl-1,3-pentylidene group, $R^2$ is 1-propyl or 2-propyl, $R^3$ is 2-propyl or 1-propyl, and $R^2$ and $R^3$ have different substituents from each other.

The glycol diester can be used as a plasticizer, a lubricant, a solvent, etc., but is not limited thereto and can be applied to any other application possible in the art.

Hereinafter, the present invention will be described in more detail with reference to the following Examples. However, these Examples are given for the purpose of illustration and are not to be construed as limiting the scope of the invention.

EXAMPLE 1

In the present Example, a 1 L glass reactor on which a distillation column filled with a packing material was mounted and to which a temperature controlling system was connected was used. 324.4 g of 2,2,4-trimethyl-1,3-pentanediol monoisobutyrate, 171.3 g of butyric acid and 3.25 g of tetraisopropyl titanate were charged into the reactor. The reactor was heated to 230° C. to perform the reaction. Water produced during the reaction formed an azeotrope with the butyric acid and was continuously removed through the distillation column on the reactor. The butyric acid separated from water was returned to the distillation column to be used in the reaction. As a result, the conversion rate of 2,2,4-trimethyl-1,3-pentanediol monoisobutyrate was 99.6% after 5 hours and the selectivity to 2,2,4-trimethyl-1,3-pentanediol monobutyrate monoisobutyrate was 95.4%.

EXAMPLE 2

The same experimental procedure as in Example 1 was performed, except that 1.47 g of tetraisopropyl titanate was used. As a result, the conversion rate of 2,2,4-trimethyl-1,3-pentanediol monoisobutyrate was 99.3% after 5 hours and the selectivity to 2,2,4-trimethyl-1,3-pentanediol monobutyrate monoisobutyrate was 95.2%.

EXAMPLE 3

In the present Example, a 3 L glass reactor on which a 15-step tray column with a diameter of 50 mm was mounted and to which a temperature controlling system was connected was used. 1373.5 g of 2,2,4-trimethyl-1,3-pentanediol monoisobutyrate, 728.5 g of butyric acid and 13.7 g of tetraisopropyl titanate were charged into the reactor. The reactor was heated to 230° C. to perform the reaction. Water produced during the reaction formed an azeotrope with the butyric acid and was included in an aqueous layer to be continuously removed through an oil water separator on the reactor. An organic layer separated from the aqueous layer was returned to the tray column (first step). As a result, the conversion rate of 2,2,4-trimethyl-1,3-pentanediol monoisobutyrate was 99.5% after 5 hours and the selectivity to 2,2,4-trimethyl-1,3-pentanediol monobutyrate monoisobutyrate was 95.3%.

EXAMPLE 4

The same experimental procedure as in Example 3 was performed, except that the reaction time was changed from 5 hours to 4 hours. As a result, the conversion rate of 2,2,4-trimethyl-1,3-pentanediol monoisobutyrate was 99.4% after 4 hours and the selectivity to 2,2,4-trimethyl-1,3-pentanediol monobutyrate monoisobutyrate was 95.8%.

EXAMPLE 5

The same experimental procedure as in Example 3 was performed, except that a 10-step tray column was used instead of the 15-step tray column. As a result, the conversion rate of 2,2,4-trimethyl-1,3-pentanediol monoisobutyrate was 99.2% after 5 hours and the selectivity to 2,2,4-trimethyl-1,3-pentanediol monobutyrate monoisobutyrate was 94.8%.

EXAMPLE 6

The same experimental procedure as in Example 3 was performed, except that a 20-step tray column was used instead of the 15-step tray column. As a result, the conversion rate of 2,2,4-trimethyl-1,3-pentanediol monoisobutyrate was 99.6% after 5 hours and the selectivity to 2,2,4-trimethyl-1,3-pentanediol monobutyrate monoisobutyrate was 95.5%.

COMPARATIVE EXAMPLE 1

In the present Example, a 1 L glass reactor equipped with a Dean-Stark trap capable of refluxing an organic layer without a distillation column was used. 291.9 g of 2,2,4-trimethyl-1,3-pentanediol monoisobutyrate, 154.6 g of butyric acid and 2.91 g of tetraisopropyl titanate were charged into the reactor. The reactor was heated to 230° C. to perform the reaction. As a result, the conversion rate of 2,2,4-trimethyl-1,3-pentanediol monoisobutyrate was 74.7% after 7 hours and the selectivity to 2,2,4-trimethyl-1,3-pentanediol monobutyrate monoisobutyrate was 92.1%.

The results obtained from Examples 1-6 and Comparative Example 1 were shown in Table 1.

TABLE 1

|  | Example 1 | Example 2 | Example 3 | Example 4 | Example 5 | Example 6 | Comparative Example 1 |
|---|---|---|---|---|---|---|---|
| Reaction time (hr) | 5 | 5 | 5 | 4 | 5 | 5 | 7 |
| Conversion rate (%) | 99.6 | 99.3 | 99.5 | 99.4 | 99.2 | 99.6 | 74.7 |
| Selectivity (%) | 95.4 | 95.2 | 95.3 | 95.8 | 94.8 | 95.5 | 92.1 |

As can be seen in Table 1, when glycol diester is prepared using methods of Example 1-6, the conversion rate and the selectivity to the glycol diester are very high and the reaction time is significantly reduced compared to when using the method of Comparative Example 1.

As described above, the method according the present invention can reduce the reaction time for synthesizing glycol diester to 6 hours or less by utilizing reactive distillation technique capable of performing both reaction and distillation and can obtain the yield of glycol diester of 95% or greater by using a Lewis acid type catalyst.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A glycol diester comprising 2,2,4-trimethyl-1,3-pentanediol mono-2-ethylhexanoate monobutyrate.

* * * * *